United States Patent [19]

Milo

[11] 4,346,519

[45] Aug. 31, 1982

[54] LIQUID LEVEL AND LIQUID CORING GAUGE

[76] Inventor: August Milo, 478 Schiller St., Elizabeth, N.J. 07206

[21] Appl. No.: 183,215

[22] Filed: Sep. 2, 1980

[51] Int. Cl.³ ............................................. G01F 23/04
[52] U.S. Cl. .............................. 33/126.4 R; 73/864.63
[58] Field of Search ................. 33/126.4 R; 73/864.63

[56] References Cited

U.S. PATENT DOCUMENTS

| | | | |
|---|---|---|---|
| 1,296,794 | 3/1919 | Haggstrom | 33/126.4 R |
| 1,539,790 | 5/1925 | Young. | |
| 1,544,206 | 6/1925 | Beard. | |
| 1,606,104 | 11/1926 | Schlueter et al. | |
| 1,638,333 | 8/1927 | Groetken. | |
| 1,947,592 | 2/1934 | Haller. | |
| 2,215,594 | 9/1940 | Parsons. | |
| 2,544,262 | 3/1951 | Hall | 33/126.4 R |
| 2,577,629 | 12/1951 | Quist | 33/126.4 R |
| 2,674,129 | 4/1954 | Cannell. | |
| 2,701,919 | 2/1955 | Anderson | 33/126.4 R |
| 2,832,145 | 4/1958 | Kious. | |
| 3,169,322 | 2/1965 | Milo | 33/126.4 R |
| 3,442,017 | 5/1969 | Frenkel. | |

OTHER PUBLICATIONS

Universal Valve Co., publication entitled "Water Level Gauge Sampler".
Lab-Line Instruments, Inc., catalog, pp. 146 and 147, showing water samplers.
W. L. Walker Co., Inc. three page brochure entitled "Tulsa Oil Thief".

Primary Examiner—William D. Martin, Jr.
Attorney, Agent, or Firm—Weiser, Stapler & Spivak

[57] ABSTRACT

The gauge includes a calibrated, elongated stick or rod to which is affixed an elongated, transparent sampler tube. A bottom valve is operable within the sampler tube and is capable of direct opening by contacting the bottom of the tank with the valve stem. The valve is also remotely operable through a cable of sufficient length to extend upwardly exteriorly of the tank for manual operation above grade level. The transparent tube extends from the bottom of the gauge stick and may be relatively short for sampling possible water contamination at the bottom of a tank or may extend several feet in length to allow core sampling throughout the entire height of the tank contents.

4 Claims, 7 Drawing Figures

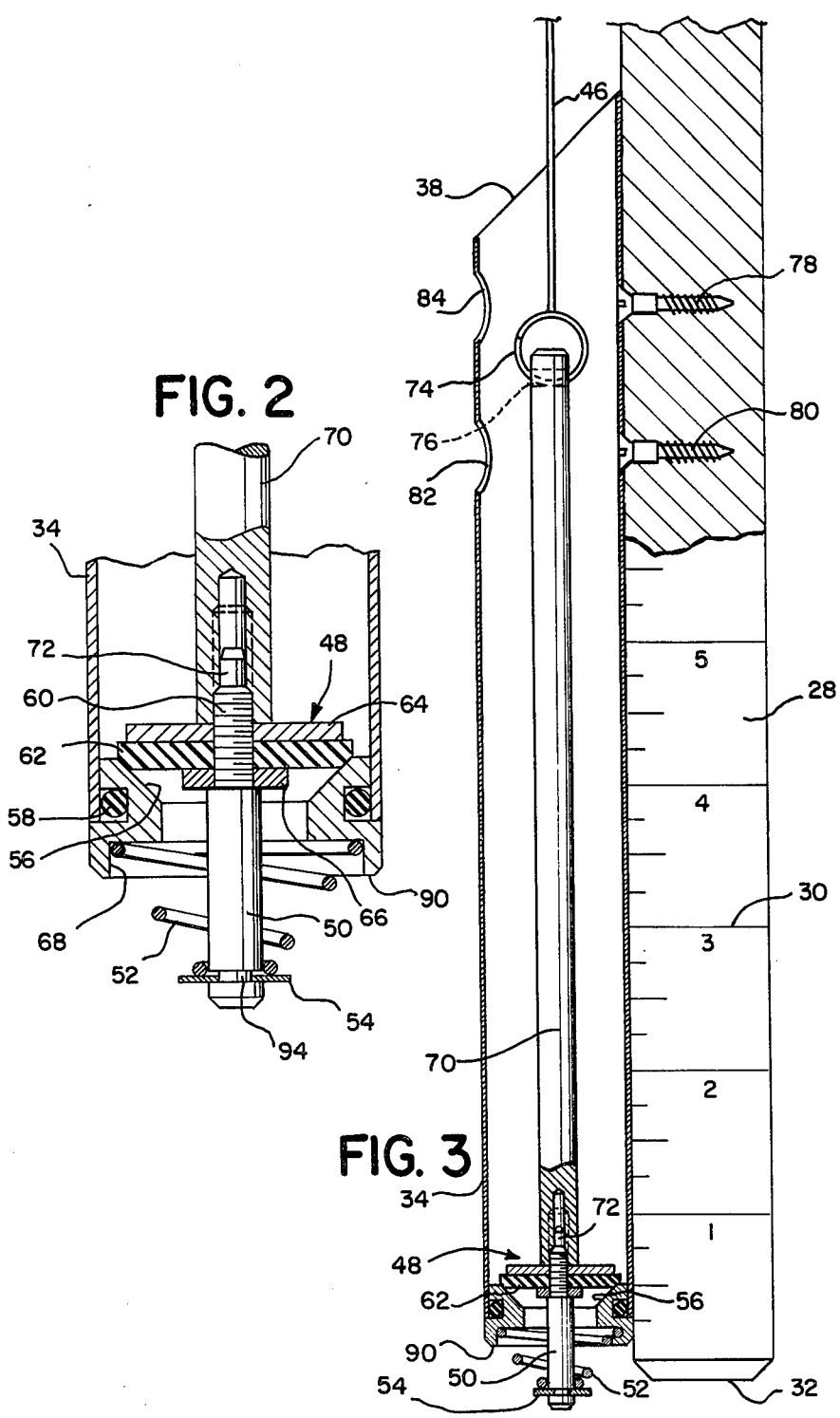

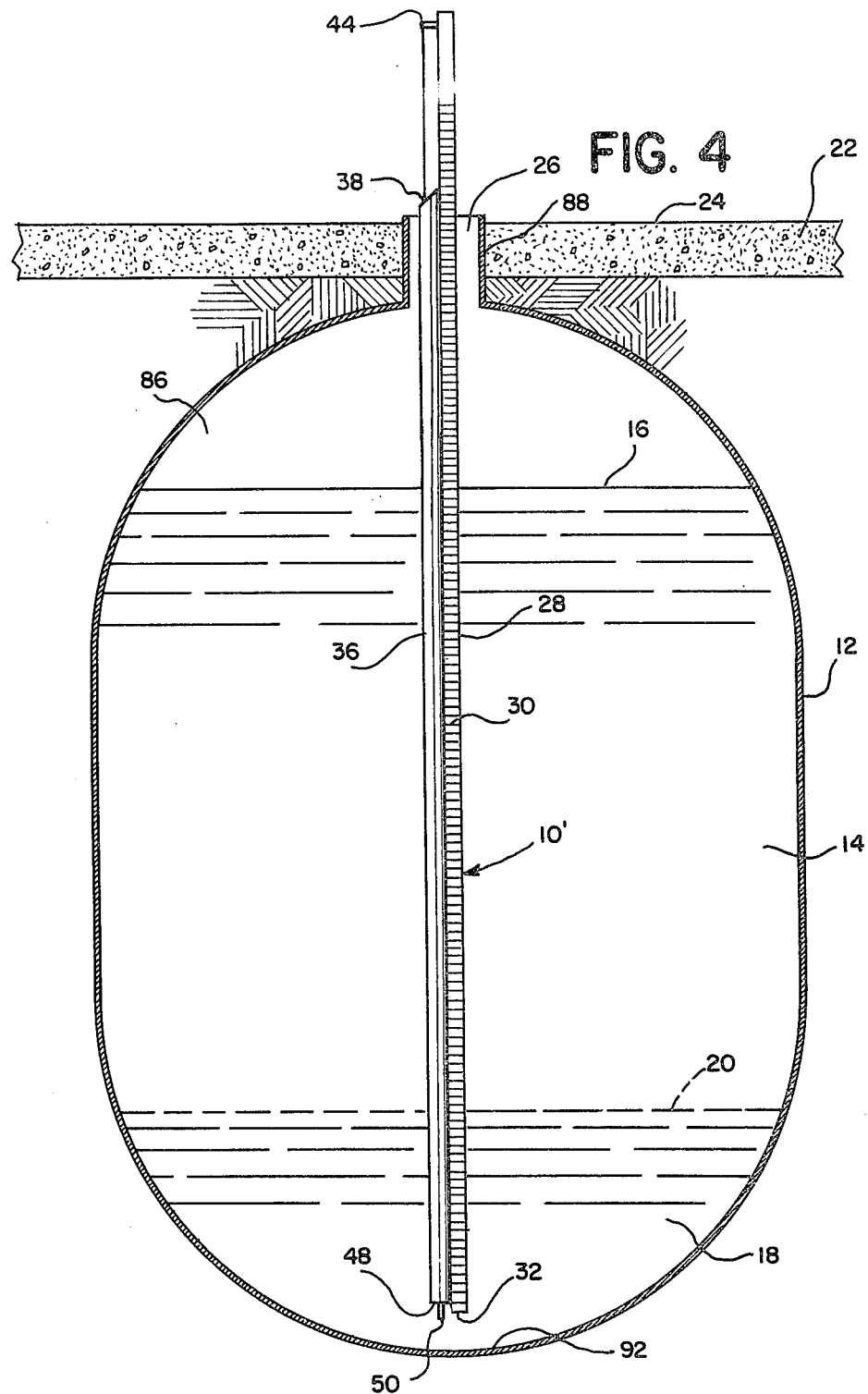

LIQUID LEVEL AND LIQUID CORING GAUGE

BACKGROUND OF THE INVENTION

The present invention relates generally to the field of gauge and tank sampler devices, and more particularly, is directed to a combination water level and liquid coring gauge.

In the field of liquid storage tanks, for example, flammable liquid storage tanks, numerous types of immersible samplers have been developed by prior workers in the art to determine information relating to interior tank conditions, such as the level of the liquid tank contents and the possible presence of contaminants, such as water within the tank. The previously available samplers also permit samples of the stored fluid to be taken from the tank for various testing purposes. Exemplary of such prior art devices are the samplers disclosed in U.S. Pat. Nos. 2,577,629, 3,169,322, and 1,606,104. Some of the prior art liquid level gauge and samplers were limited in scope and were capable of functioning only at the bottom of the tank. Others were deficient in that they were relatively short in length and accordingly, were effective in sampling or gauging only a limited strata of the tank contents. Some of the previously available prior art devices were not capable of giving easy, quick visual indications of the interior tank conditions.

The water level and liquid coring gauge of the present invention overcomes the deficiencies of the earlier designs and further is designed to speed tank quantity measuring operations by providing a visual sample in immediate juxtaposition to the gauge calibrations of a dipstick. By incorporating the ability to take liquid level samples, rather than simply employing the dipstick to determine the level of the wetted area, increased efficiency and speed are achieved inasmuch as the operator need no longer wait for the liquid of one tank to evaporate from the dipstick before testing the additional tanks in a series of tanks.

SUMMARY OF THE INVENTION

The present invention relates generally to the field of tank liquid quantity measuring and sampling devices, and more particularly, is directed to a see-through type water level and liquid coring gauge of the type set forth.

The liquid sampling gauge of the present invention includes an elongated wooden, metallic or plastic measuring stick or rod of known type of suitable length to extend from exteriorly of a tank to the bottom thereof for liquid measuring purposes. The stick includes usual graduations or vertically spaced indications to provide a relatively accurate reading at all liquid levels interiorly of the tank.

A liquid sampler tube is affixed to the tank measuring stick and the tube extends upwardly from the bottom of the stick. In one embodiment, the sampler tube can be relatively short, for example, six or eight inches or so in length to determine the presence and quantity of a contaminant such as water, near the bottom of the tank. In another embodiment, the sampler is fabricated of a relatively long tube and extends vertically along the gauge stick a distance equal to the interior height of the tank to thereby provide means for core sampling throughout the entire height of the liquid contents of the tank. The liquid sampler assembly includes a bottom positioned valve which is directly operable either interiorly of the tank through a bottom extending stem or is remotely operable from the exterior of the tank through an operating string or cord which can be manually pulled to open the valve at any vertically oriented position of the sampler tube within the tank.

The measuring stick and sampler constructions are fabricated of materials compatible for use in the environmental conditions present within the tank to be sampled. For example, if the material contained within the tank is gasoline, then all components should be fabricated of materials suitable for use within a gasoline atmosphere. Similarly, if the sampler is to be used within a corrosive or other such hostile environment, due care should be taken to employ materials of construction that will be suitable for long use under these conditions without breakdown, wear or other deterioration. It is to be understood that the invention of the present sampler resides in its ability to measure liquid level and to extract liquid core specimens in any strata within a tank and the invention is not limited to particular liquids or to specific materials of construction. Accordingly, the descriptive terms employed throughout are to be broadly construed as to scope and meaning.

It is therefore an object of the present invention to provide an improved liquid height and liquid coring gauge of the type set forth.

It is another object of the present invention to provide a novel liquid height and liquid coring gauge including a valve which is capable of proximate operation from within the tank and remote operation from without the tank.

It is another object of the present invention to provide a novel liquid height and liquid coring gauge which includes in combination a graduated measuring stick and a plastic see-through sampler tube together with remote operating means to selectively admit liquid samples into the interior of the tube.

It is another object of the present invention to provide a novel water level and liquid coring gauge including a wooden gauge pole having height graduations throughout its length and an affixed transparent sampler tube including a remotely controlled valve and valve opening means extending the full length of the gauge pole to a remote location exteriorly of the tank.

It is another object of the present invention to provide a novel liquid height and coring gauge comprising in combination stick gauging means including measured graduations indicated thereon, core sample means affixed to the stick gauging means, valve means associated with the sampler means to selectively admit liquid samples interiorly of the sampler means and operating means remote from the valve means to selectively open the valve means to admit liquid samples into the sampler means.

It is another object of the present invention to provide a novel liquid height and liquid coring gauge that is simple in design, inexpensive in manufacture and trouble free when in use.

Other objects and a fuller understanding of the invention will be had by referring to the following specification and claims, taken in conjunction with the accompanying drawings wherein like reference characters refer to similar parts throughout the several views and in which:

BRIEF DESCRIPTION OF THE DRAWINGS

FIG. 2 is an enlarged, partial, cross sectional view taken along line 2—2 on FIG. 1, looking in the direction of the arrows.

FIG. 3 is an enlarged, partial, sectional view through a sampler affixed to a gauge stick, portions of which are broken away to expose interior construction details.

FIG. 4 is a cross sectional view similar to FIG. 1, showing a second embodiment of a liquid height and liquid coring gauge.

DESCRIPTION OF THE PREFERRED EMBODIMENT OF THE INVENTION

Figure 1:
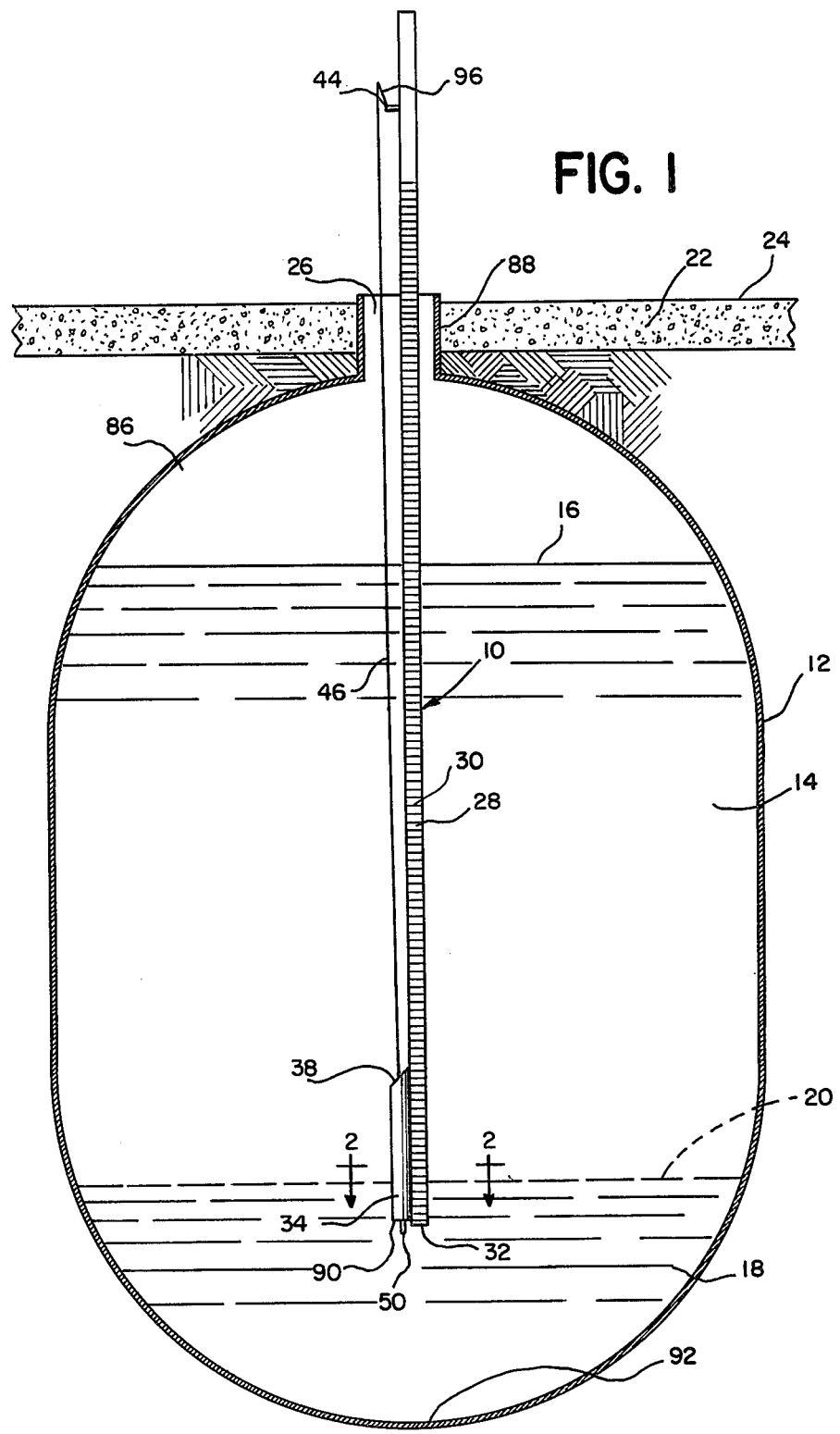
FIG. 1 is a cross sectional view showing a first embodiment of the liquid height and liquid coring gauge in use within an underground liquid storage tank.

Although specific terms are used in the following description for the sake of clarity, these terms are intended to refer only to the particular structure of the invention selected for illustration in the drawings and are not intended to define or limit the scope of the invention.

Referring now to the drawings, there is illustrated in FIG. 1 a liquid sampling assembly generally designated 10 in use within an underground liquid storage tank 12 of the type suitable to store or retain a flammable liquid, for example, gasoline 14. As illustrated, the tank 12 is installed below the ground surface 24 and a concrete slab 22 may be provided over the tank 12 in the usual manner for safety purposes in accordance with national and local safety codes. While the tank is shown positioned immediately below the concrete slab 22, it will be appreciated that various safety codes in different localities may require more or less depth between the top of the tank and the ground surface 24. Accordingly, the distance shown is illustrative only. A manhole or handhole or other tank opening 26 communicates the interior 86 of the tank with atmosphere above the ground surface 24 through a conventional standpipe 88. In practice, it is usual to provide a removable cover (not shown) to prevent unauthorized entrance or tampering with the interior contents of the tank 12.

The liquid sampling assembly 10 comprises generally an elongated stick or rod 28 which preferably is a conventional stick gauge as commonly employed in and about gasoline service stations for insertion into the underground tanks for liquid content measuring purposes. The gauge stick 28 includes a plurality of spaced graduations 30 in well known manner and the graduations 30 preferably extend the entire length or height of the gauge stick 28. While most presently available gauge sticks 28 are usually fabricated of wood, it will be appreciated that other materials such as metal or plastic may also be similarly employed in the event that the liquid contents within the tank 12 were of such nature as to adversely affect a wooden gauge pole.

Referring now to FIGS. 1–3, a hollow, cylindrical sampler 34 which preferably is fabricated of a transparent or translucent material, for example, a suitable clear plastic such as polyethylene is affixed to the gauge stick 28 by a pair of threaded fasteners 78, 80. Horizontally aligned access openings 82, 84 are provided through the sampler body sidewall to facilitate driving the fasteners 78, 80 into the gauge pole 28. Preferably, the bottom 90 of the sampler tube 34 is positioned substantially adjacent to the bottom 32 of the gauge stick 28 so that the sampler 34 can be extended into the tank 12 down to the bottom 92 thereof for bottom sampling purposes. The sampler tube 34 terminates upwardly in an inclined sloping surface 38 to facilitate removal of the sampling assembly 10 after use and to prevent engagement of the top of the sampling tube with the bottom of the standpipe 88.

Referring now particularly to FIGS. 2 and 3, a valve assembly 48 is operably positioned at the bottom of the sampler tube 34 and includes a valve seat 56 which is a press fit within the open bottom of the sampler tube as illustrated. An O-ring gasket 58 is employed in known manner to prevent leakage about the seat 56 after removal of the sampling assembly 10 from within the tank 12 to maintain the integrity of sampler accuracy. A resilient washer 62 is normally urged into sealing engagement against the valve seat 56 by action of the coil spring 52.

Still referring to FIGS. 2 and 3, the resilient washer 62 is maintained in place upon a valve stem 50 intermediate a nonresilient washer 66 and a retainer washer 64, which washers 64, 66 may be threadedly or otherwise engaged upon the threaded stem 60 of the valve stem 50. The valve stem 50 is provided with an endward circular groove 94 within which is seated a split spring retainer 54 to provide an outer terminus for the spring 52. The valve seat 56 terminates downwardly in a recessed socket 68 within which the inner end of the spring 52 is retained. The outer or second end of the spring 52 biases against the top of the spring retainer 54 as illustrated to normally urge the resilient washer 62 tightly against the valve seat 56, to prevent passage of liquid through the valve 48.

The valve stem 50 extends downwardly below the bottom 32 of the gauge rod 28 whereby the valve stem 50 can be functioned to contact the bottom 92 of the tank 12 by dropping the gauge stick or meter stick 28 downwardly as far as possible. In this position, the tank bottom 92 acts to push the valve stem upwardly against the bias of the spring 52 to thereby lift the resilient washer 62 from the valve seat 56 and thus open the valve 48 for liquid sampling purposes. Accordingly, the valve 48 can be proximately opened within the tank through interaction of the tank bottom 92 and the bottom of the valve stem 50 to secure a sample of the liquid tank contents from near the bottom of the tank. For example, if an impure liquid 18, for example water, was to inadvertently be admitted into the interior 86 of the tank 12, the impure liquid 18 would collect near the bottom up to its volumetric tank level which is shown schematically as the surface line 20. In such a situation, the interaction of the valve stem 50 and the tank bottom 92 would cause a sample of the impure liquid 18 to enter the sampler tube 34, which upon removal from the tank, would advise the operator (not shown) of the presence of such an impurity.

Additionally, it is an important feature of this invention to permit remote function of the valve 48 by utilizing a cord or string 46 which extends from the valve actuator rod 70 upwardly along the meter stick 28, through the standpipe 88 to above the ground surface 24 for manual remote operation above ground surface in the manner hereinafter more fully set forth. The actuator rod 70 connects to the valve stem 50 in a manner to pull the valve stem 50 upwardly in response to upward forces imposed upon the cord 46. In one embodiment, the actuator rod 70 may be provided with a bottom, threaded socket 72 to threadedly engage the threaded extension 60 of the valve stem 50. As illustrated in FIG. 3, the actuator rod 70 is upwardly provided with a cross hole or bore 76 within which is positioned a connector ring 74. The cord or string 46 is tied or otherwise secured to the connector ring 74 in a known, permanent type interconnection.

As best seen in FIG. 1, the upper terminus 96 of the cord 46 is tied, knotted or otherwise secured to the stationary connector 44 which is provided near the upper end of the meter or gauge rod 28. The cord 46 extends vertically from the connector ring 74 and terminates in a permanent connection at the upper string fixed connector 44. Accordingly then, the resilient washer 62 may be conveniently urged upwardly away from the seat 56 by pulling transversely outwardly or upwardly on the cord 46 as illustrated to open the valve 48. Release of the cord of string 46 will allow the natural bias of the spring 52 to automatically return the resilient washer 62 into sealing engagement with the valve seat 56 to again close the valve 48.

It will be appreciated that the present invention has been described for use in connection with a flammable liquid, such as gasoline 14 contained within the interior of an underground storage tank 12 with an impure liquid, such as water 18, illustrated at the bottom of the tank. Of course, other liquids, either flammable or non-flammable, alone or in combination and perhaps water or other liquid or semi-liquid impurities could be present within the interior of the tank 12. Accordingly, differing construction components of the gauge rod 28, the sampler tube 34 and the valve 48 may be required, depending upon the nature of the stored liquid.

Under the circumstances, the construction materials employed should be compatible for use within the environment of the actual liquid or liquids present and all such materials are considered to be within the scope and intent of the present invention. As above set forth, the gauge rod 28 could preferably be constructed of wood, as most commonly employed. However, in the event that the liquid within the tank was hostile to wood, then another material, such as a suitable plastic in elongate form could optionally be employed. Further, it is preferable to fabricate the sampler tube 34 of a clear plastic material to facilitate a visual observation of the liquid contents and liquid level therewithin. If plastic could not be conveniently employed due to the characteristics of the stored liquids, other materials, such as glass could be cemented, strapped, or otherwise affixed near the bottom of the meter stick 28. If necessary, for example if the stored liquid was detrimental to cord or string, the pull cord 46 could be fabricated of any elongate, flexible material, such as steel cable, chain, plastic cord or other material suitable for the use which would not be adversely affected by the properties of the stored liquid within the interior of the tank 12.

Referring now to FIG. 4, it will be observed that the tank 12 is similar in construction and content to the tank illustrated in FIG. 1 and includes gasoline 14 stored within the tank up to its top level 16. An impurity such as water 18 is illustrated at the bottom of the tank and the level line 20 indicates the interface between the impure liquid 18 and the pure gasoline 14. In this embodiment, the sampler tube 36 is fabricated similar to the short sampler tube 34 except that the tube extends in height a distance at least equal to the height of the tank itself. The elongated sampler tube 36 is provided at its bottom with a valve 48 having a bottomly extending valve stem 50 for proximate operation in the manner hereinbefore set forth. Similarly, the valve 48 can be remotely operated by use of a flexible cord 46 which functions similarly to the cord 46 of FIG. 1 and which is upwardly secured to the fixed connector 44 for remote operation of the valve 48 from above ground level in the manner hereinbefore set forth.

Preferably, the elongated sampler tube 36 is also fabricated of transparent plastic material to facilitate ready visual observation of the sampler tube contents when the modified liquid sampling assembly 10' is removed from the interior of the tank 12. By employing remote valve operation made possible by use of the actuator rod 70 and the upwardly extending cord 46, the valve 48 can be opened at any time during submersion of a sampler tube 34 or 36 within the liquid contents 14, 18 of the tank 12. Thus, a sample at any particular vertical height within the tank 12 can be taken by pulling on the cord 46 to lift the actuator rod 70, thereby enabling the operator to sample and know exactly the contents of the stored liquid at any particular horizontal strata within the tank 12.

Further, the valve 48 can be opened before the liquid sampling assembly 10', is lowered into the tank through the standpipe 88. With the resilient washer 62 removed or pulled away from association with the valve seat 56, a complete cross-sectional sampling or core of the tank contents, for example gasoline 14, bottom water 18, and any other impurities (not shown) can be taken. In the event a liquid such as gasohol was retained within the tank 12, the sampling apparatus of the present invention, when employed to extract a core sample, will provide a visual check for any visible phase separation which may have occurred.

Under the circumstances, when considering the embodiment illustrated in FIG. 4, the long length of the sampler tube 36 allows the operator the option of testing the entire vertical contents of the tank by removing a core sample to visually indicate the interior conditions at each level or strata within the tank. By employing a transparent sampler tube 34 or 36, the transparency provides the advantage of allowing visual inspection of the core sample directly through the walls of the tube in a speedy and unencumbered manner.

When employing the device as a water level indicator, preferably a core sample can be taken with the modified liquid sampling assembly 10' of FIG. 4 to thereby quickly show within the elongated sampler tube 36 the exact level of the liquid contained within the tank. Direct reading can be made at the adjacent graduations 30 which are inscribed or otherwise provided on the gauge rod 28. In this manner, a much faster reading can be made than was previously possible when employing the former practice of simply dropping the gauge stick into the tank opening 26. When using the apparatus of the present invention, the operator need no longer be concerned with indistinct wet marks on a wooden gauge rod of the prior art in order to note the liquid level. Further, when gauging the liquid contents of a number of tanks, which is most usual in normal gasoline service station operation, the operator need not now wait until the liquid from one tank evaporates from the gauge stick before he is able to test the next in a series of tanks. By utilizing the liquid sampling assembly 10' of this invention, the operator can now merely dump the contents of a first tank from the elongated sampler tube 36 by pulling on the string 46 after he has made his reading and the device can then be immediately inserted into the next adjacent tank to quickly determine the contents level in the second tank without waiting.

By employing the liquid sampling assembly 10 in the manner illustrated in FIG. 1, a sampling can be limited to any preselected level by lowering the sampler tube 34 to the desired level by reading the gauge stick graduations 30 at the ground surface 24 as the meter stick 28 is lowered into the tank 12. Once a desired level is reached, the valve can be operated anywhere within the tank 12 by pulling on the string 46 to lift the resilient washer 62 away from its accompanying seat 56, thus allowing an inflow of material at that level. After a proper sample has been taken, the cord 46 is released and the valve will automatically close under the bias of the spring 52 to thereby preserve the integrity of the sample as it is brought to the surface. In view of the foregoing, it will be appreciated that the liquid level and liquid coring gauge of the present invention is substantially universal in operation in that the same device can be equally employed for core sampling, bottom sampling, sampling at any intermediate elevated height within the tank as may be determined by the operator and for liquid level indication.

Figure 5:
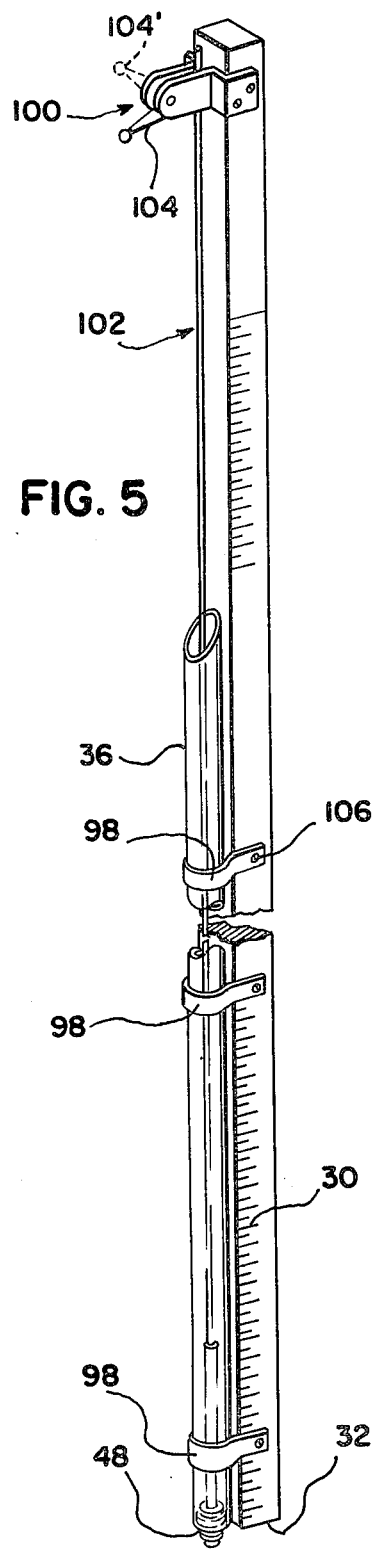
FIG. 5 is a perspective view of a modification of the liquid height and liquid coring gauge of FIG. 4.

Referring now to FIG. 5, a modified embodiment of a liquid sampling assembly is illustrated which comprises generally a conventional gauge pole 28 to which is affixed an elongated sampler tube 36', which preferably is fabricated of a clear plastic of suitable properties to be unaffected by repeated insertions into a tank containing gasoline 14 or other liquid. A plurality of mounting straps 98 exteriorly affix the tube 36' to the gauge pole 28 in vertically spaced relationship by employing conventional fasteners 106. The embodiment of FIG. 5 includes a remote valve operator 100 which is designed to free both of the operator's hands to provide increased facility in the manipulation of the gauge stick 28. The remote valve operator comprises an operating lever 104 in operative engagement with a rigid rod 102 of diameter small enough to conveniently operate within the tube 36'. The operating lever 104 and the operating rod 102 cooperatively act as a remote valve opening device.

The lever assembly 104 is preferably mounted near the top of the gauge stick as illustrated to permit easy accessibility exteriorly of the tank 12. The rigid rod 102 connects at its lower end to the actuator rod 70 and terminates upwardly in a pivotal connection at the inner end of the operating lever 104. When the lever 104 is in the "closed" position as illustrated in dotted lines, the valve 48 is closed and sealed. When the operator (not shown) wishes to sample the contents of the tank 12, he can simply move the lever 104 to the "open" position as shown in solid lines. In so doing, the lever 104 pivots the rigid rod 102 upwardly, thereby opening the valve 48. The lever assembly includes an interior detent dimple (not shown) of known design to maintain the valve 48 in the "open" position without operator assistance. The operator (not shown) can easily close the valve 48 when desired by pivotally rotating the lever with sufficient force to overcome the frictional engagement of the detent dimple to the "closed" position. It will be noted that the bias of the spring 52 aids in closing the valve 48 as the lever moves about its pivot toward the "closed", dotted line position illustrated.

Figure 6:
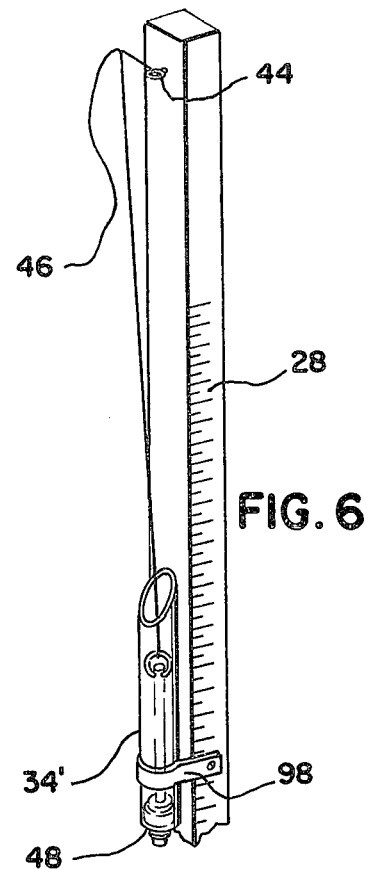
FIGS. 6 and 7 illustrate perspective views of a modification of the liquid height and liquid coring gauge of FIG. 1.
Figure 7:
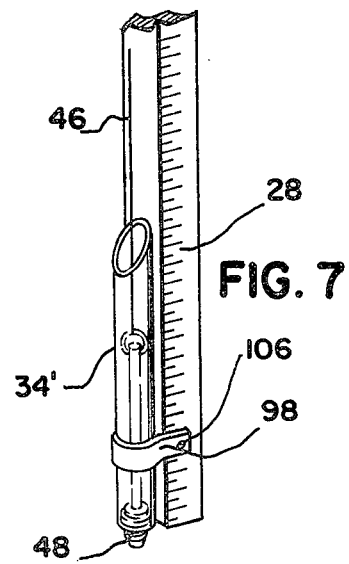

As illustrated in FIGS. 6 and 7, in order to sample the contents at any particular stratum of the stored liquid in the tank 12, the mounting of the short tube sample 34' to the gauge stick 28 may be adjustable by the use of a plurality of longitudinally spaced mounting straps 98. In this embodiment, the short tube sampler 34' may be constructed without the horizontally aligned access openings 82, 84, as was previously required. As shown in FIG. 6, the cylindrical sampling tube 34' can be mounted at any desired position along the length of the gauge stick 28 by the one or another of the mounting straps 98. The straps 98 should be fabricated of a material suitable for the liquid environment to be sampled. It is contemplated that the straps could be metallic, plastic or ceramic as may be required to withstand attack by the particular liquid stored within the tank 12.

In use, the operator (not shown) mounts the short sampling tube 34' at a predetermined position on gauge stick 28 by securing the sampler tube with a properly positioned mounting strip 98 before immersing the modified liquid sampling assembly 10" into the tank 12. When the bottom 32 of the gauge stick 28 approaches the bottom of the tank 12, the operator then manually opens the valve 48 either by pulling on the cord 46 as illustrated in FIG. 6 or by rotating the lever 104 in the embodiment of FIG. 5.

After the desired sample is contained within the sampler tube 34', the valve is allowed to close by releasing the upward force on the string 46 or by rotating the lever 104 to its dotted line, closed position (FIG. 5). After removing the sampling assembly 10" from the tank 12, the operator can examine the contents of the sampling tube 34' and determine the exact depth of the stratum from which the contents were taken by reading the graduations 30 on the gauge stick 28 adjacent to the sampling tube.

Although the present invention has been described with reference to the particular embodiments herein set forth, it is understood that the present disclosure has been made only by way of example and that numerous changes in the details of construction may be resorted to without departing from the spirit and scope of the invention. Thus, the scope of the invention should not be limited by the foregoing specification, but rather only by the scope of the claims appended hereto.

What is claimed is:

1. In a liquid gauge suitable for sampling the liquid contents of a tank of the type including a top opening and a bottom, the combination of gauge stick means of sufficient length to extend from the bottom of the tank through the top opening to measure liquid levels within the tank;

liquid sampling means affixed to the gauge stick means to remove a liquid sample from the tank, the liquid sampling means comprising a hollow, elongate sample tube; and valve means positioned in the sampler tube and being movable between open and closed positions to alternately allow liquid to pass therethrough when in the open position and to prevent passage of liquid when in the closed position, the valve means comprising a seat, a valve stem, a spring and a washer, the washer being normally urged toward the seat by the spring to move the valve means to the closed position and the washer being movable away from the seat against the bias of the spring to move the valve means to the said open position, the valve means further comprising a stem including threaded and unthreaded portions, a first actuator comprising a rod connected to the threaded stem portion and extending within the sample tube and away from the seat and a remote valve operator connected to the first actuator in spaced relation from the washer and extending in length a distance greater than the height of the tank, the remote valve operator extending through the top opening when the sampler tube is positioned near the bottom of the tank;

whereby the valve means may be moved to the said open position by pulling the remote valve operator from a position exteriorly of the tank.

2. The gauge of claim 1 wherein the valve means further comprises a second actuator connected to the stem, the second actuator being adapted to move the washer away from the seat, the second actuator comprising a stem extension, the stem extension extending below the washer and below the bottom of the gauge stick means, whereby the valve means may be moved to the open position either by striking the second actuator upon the tank bottom or by function of the said remote valve operator.

3. The gauge of claim 2 wherein the second actuator, the first actuator and the stem are secured together in linear alignment and substantially concentric within the sample tube.

4. The gauge of claim 2 wherein the remote valve operator comprises an operating lever, the lever being pivotal between valve open and valve closed positions and wherein the operating lever is equipped with a detent to maintain the lever in at least one of its said positions.

* * * * *